United States Patent [19]

Kida

[11] Patent Number: 5,412,477
[45] Date of Patent: May 2, 1995

[54] APPARATUS FOR MEASURING BEND AMOUNT OF IC LEADS

[75] Inventor: Tomoyuki Kida, Tokyo, Japan
[73] Assignee: NEC Corporation, Tokyo, Japan
[21] Appl. No.: 18,864
[22] Filed: Feb. 17, 1993
[30] Foreign Application Priority Data
   Feb. 18, 1992 [JP]  Japan .................................. 4-029828
[51] Int. Cl.⁶ ................................. G06K 9/00
[52] U.S. Cl. ................... 356/394; 382/145; 348/135
[58] Field of Search .................. 359/370, 371; 29/834, 29/739, 740, 741; 356/354, 355, 356, 358, 394; 382/8, 21, 27, 41, 49; 358/101, 106, 107

[56] References Cited

U.S. PATENT DOCUMENTS

| 4,995,157 | 2/1991 | Hall | 29/834 |
| 5,007,097 | 4/1991 | Mizuoka et al. | 382/8 |
| 5,168,528 | 12/1992 | Field, Jr. | 382/1 |
| 5,249,239 | 9/1993 | Kida | 382/8 |
| 5,259,042 | 11/1993 | Matsuki et al. | 382/50 |

FOREIGN PATENT DOCUMENTS 0136707  5/1990  Japan .
475359A 10/1992  Japan .

*Primary Examiner*—Robert P. Limanek
*Assistant Examiner*—David B. Hardy
*Attorney, Agent, or Firm*—Whitham, Curtis, Whitham & McGinn

[57] ABSTRACT

A lead-bend measuring apparatus comprising: an illuminating device for projecting light onto leads projecting from a package of an integrated circuit device; an imaging device for imaging light reflected from and transmitted through the leads; a cutout device for fetching an image of the imaged light and dividing the image into a plurality of sections; a binarization processing device for processing gradations of the image with different binarization levels for each of the divided sections; a profile counter device for preparing profiles of various portions of the leads corresponding to the respective sections from binarized data subjected to processing by the binarization processing device; a calculating device for calculating a deviation of each of the prepared profiles from a reference profile and determining an amount of bend of each of the leads; and a device for determining a non-defective or defective state by making a comparison between the amount of bend calculated and allowable values. The respective sections are processed by corresponding binarization levels to measure the bend of leads, so that clear binarized images are obtained even if the illuminance of the various portions of the leads is not uniform.

20 Claims, 9 Drawing Sheets

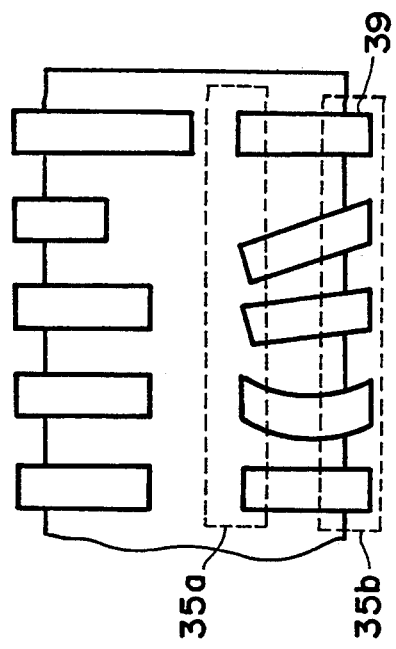
FIG. 4A PRIOR ART
FIG. 4B PRIOR ART
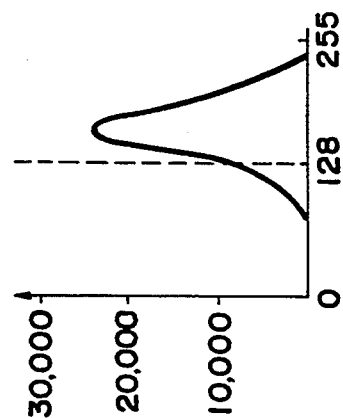
FIG. 4E PRIOR ART
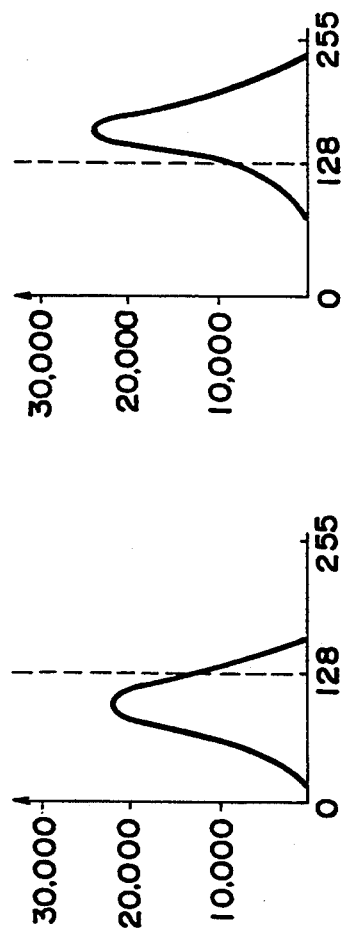
FIG. 4C PRIOR ART
FIG. 4D PRIOR ART
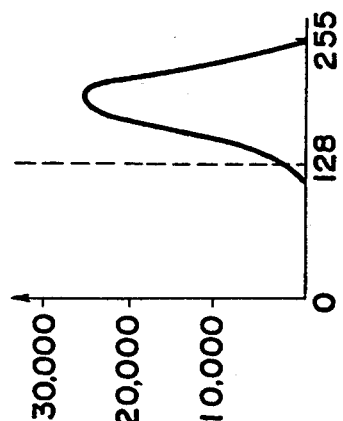
FIG. 4F PRIOR ART
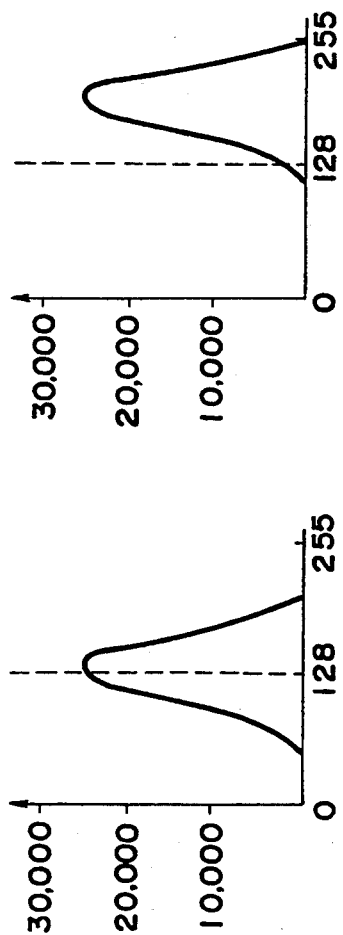
ORDINATE: DEGREES
ABSCISSA: GRADATIONS

APPARATUS FOR MEASURING BEND AMOUNT OF IC LEADS

BACKGROUND OF THE INVENTION (1) Field of the Invention

The present invention relates to a lead-bend measuring apparatus for measuring an amount of bend of leads projecting from a package of an integrated circuit device (hereafter simply referred to as an "IC") so as to determine the non-defective or defective state of the product by comparing the measured results with allowable values.

(2) Description of the Related Art

FIG. 1 is a block diagram of a lead-bend measuring apparatus which shows a conventional example. As shown in the drawings, the lead-bend measuring apparatus of this type conventionally comprises an inspection stage 38 on Which an IC 2 is placed with its rear surface facing up by means of clamp claws 3a, 3b and 3c; a pair of annular incandescent lamps 4a for projecting light onto distal ends, proximal ends, and apex portions of the leads of the IC 2 as well as a pair of optical fiber arrays 4b connected to an incandescent lamphouse; a pair of camera heads 1, a camera driver 10, and a camera controller 11 for fetching the light reflected from and transmitted through the leads and for imaging the distal ends, proximal ends, and apex portions of the leads; an A/D converter 13 for fetching image signals from the camera controller 11 by means of a fetch clock 12 and converting the same into 256 gradations; a frame memory 15 for storing the image data converted into 256 gradations; a CPU 23 adapted to fetch the image data from the frame memory 15, divide the fetched image data into a plurality of sections, binarize the image data of the divided sections, prepare a profile of various lead portions by means of this binarized data and calculate a deviation of that profile from a reference profile to determine an amount of bend of each lead, and compare this amount of bend with allowable values so as to determine the non-defective or defective state; a printer 29, a CRT 28, a keyboard 27, and an external storage device 26 for storing the allowable values and the like, all of these units being connected to the CPU 23 via I/O ports 14f; a binary image memory 18 for temporarily storing the image data subjected to binarization processing by the CPU 23; a feeding section 6 for feeding ICs 2; a horizontal transport mechanism section 5 for transporting the ICs to a non-defective storing section 7 or a defective storing section 8 after the non-defective or defective state of the ICs is determined by the CPU 23; and a sequencer 9 for controlling the various units.

The CPU 23 comprises an area cutout unit 16 for fetching the image data of the entire imaged regions of the leads of the IC 2 from the frame memory 15 via I/O ports 14b, and for dividing the fetched image data into a plurality of divided regions designated by area-designating-pointer storage units 19a; a binarization processing unit 17 for binarizing the image data of the entire divided sections at a binarization level stored in advance in a binarization-level storage unit 20a, and for storing the binarized data in the binary image memory 18 connected to an external device via I/O ports 14d; a profile counter 21 for fetching the binarized data from the binary image memory 18 via I/O ports 14e and preparing an image profile of the leads; an area center-of-gravity calculating unit 22 for calculating the center of gravity of an area of the prepared profile; a lead-bend-amount calculating unit 25 for calculating a deviation of the center of gravity of the area from a reference profile position so as to obtain an amount of bend; and a non-defective/defective determining unit 24 for determining the non-defective or detective state by comparing this amount of bend and allowable values stored in advance.

Next, a description will be given of the operation of this lead-bend measuring apparatus. First, the IC 2 is fed from the feeding section 6 to the inspection stage 38, and the IC 2 is placed on the inspection stage 38 with its rear surface facing up. The IC 2 is then fixed to the inspection stage 38 by means of the clamp claws 3a, 3b and 3c. Subsequently, light is projected onto the distal ends, proximal ends, and apex portions of the leads by means of the annular incandescent lamps 4a and the optical fiber arrays 4b. The camera heads 1 fetch the light reflected from or transmitted through the various portions of the leads and effect imaging. The camera controller 11 fetches imaging signals by means of the fetch clock 12, and the imaging signals are divided into 256 gradations by the A/D converter 13 and are stored in the frame memory 15. The area cutout unit 16 then divides all the image data of the frame memory 15 into a plurality of designated sections stored in advance in the area-designating-pointer storage units 19a. Subsequently, the binarization processing unit 17 effects binarization processing of all the image data of the areas divided by using one binarization level which is set in advance in the binarization-level storage unit 20a. The image data subjected to binarization processing is temporarily stored in the binary image memory 18. The profile counter 21 fetches the image data from the binary image memory 18 through the I/O ports 14e and prepares profiles of various portions of the leads.

A description will now be given of a method of calculating an amount of bend of each lead from the profiles of the various portions of the leads. FIG. 2 is a diagram illustrating an algorithm for calculating an amount of bend in the lead-bend measuring apparatus shown in FIG. 1. FIGS. 3A to 3C are flow-charts illustrating the algorithm. If it is assumed that the profile of each portion is depicted as shown in FIG. 2, in Step 310 of FIG. 3A, WINDOWs 1 and 2 shown in FIG. 2 are set by the area center-of-gravity calculating unit 22 and the lead-bend-amount calculating unit 25. Then, points a, b, c and d at which defining lines of the WINDOWs 1 and 2 and contour lines of the profile intersect each other are determined in Step 320. In Step 330, mid-points between the respective pairs of points of intersection are determined and set as WG1 and WG2. In Step 340, an angle $\theta$ of inclination of the profile, i.e., an angle of bend, is determined from X-Y coordinate values of WG1 and WG2. In Step 350, coordinates of a mid-point STP at one end of the profile are determined. Here, the coordinates of STP are calculated as shown in FIG. 3B. Namely, in Step 351 of FIG. 3B, a segment is extended from WG1 in parallel with the Y-axis. Then, in Step 352, the length of a segment A between the point WG1 and a point WG1VP is calculated. A segment B is determined from the segment A in Step 353. Then, the coordinates of STP are calculated in Step 354.

Subsequently, in Step 360 of FIG. 3A, coordinate values of a mid-point SBP at the other end of the profile are determined in a similar manner in accordance with the flow-chart shown in FIG. 3C. Then, in Step 370 of FIG. 3A, the difference between the X-axis components of the mid-points STP and SBP is calculated as the amount of bend.

Next, in the non-defective/defective determining unit 24, allowable values of bend stored in advance in the external storage unit 26 are extracted, and a comparison is made between the same and the calculated amount of bend so as to determine the non-defective or defective state. Then, the horizontal transport mechanism section 5 is actuated by the sequencer 9, and the IC 2 whose non-defective or detective state has been determined is stored in the non-defective storage section 7 or the defective storage section 8. The inspection of the bend of IC leads has hitherto been effected automatically in the above-described manner.

However, since the lead of the IC is complicated in shape, and the finished state of the surfaces of the leads is not necessarily uniform, it is impossible to obtain uniform intensity of light reflected from the various portions of the leads. As a result, the visibility of the projected images of various portions of the leads differs for each section, which in turn results in measurement errors, making it difficult to effect accurate measurement.

FIGS. 4A to 4F are diagrams for explaining the problems in the conventional lead-bend measuring apparatus, in which FIGS. 4A to 4D are graphs illustrating the distribution of illuminance at gradations, and FIGS. 4E and 4F are diagrams illustrating the positions of sections in the leads. A description will now be given of the aforementioned problems with reference to the drawings. For instance, as shown in FIGS. 4E and 4F, if leads 39 are illuminated with light at sections 35a, 35b, 35c and 35d, the distribution of illuminance differs for each of these sections, as shown in FIGS. 4A to 4D. Here, the sections 35a and 35b are imaged by one camera, and the sections 35c and 35d are imaged by another. With the conventional lead-bend measuring apparatus, since the binarization processing of the image data of all of these sections is performed at only one binarization level, not all the sections exhibit the same visibility. That is, as for the distribution of illuminance in the sections 35b and 35d respectively shown in FIGS. 4B and 4D, peaks are located closer to the high gradation side with gradation 128 in the binarization processing level serving as a boundary, so that images of the same illuminance are obtained when the image data is processed at the same binarization level. However, in a case where the distribution of illuminance utterly differs in the sections 35a and 35c respectively shown in FIGS. 4A and 4C, if the image data is processed at the same binarization level, it is impossible to obtain clear binarized images thereof. In other words, in the image subjected to binarization processing, an area which should essentially be recognized as a bright spot is recognized as a dark spot. That is, the imaged portion of the lead is recognized as an image which is more reduced than the actual size. Hence, there is a problem in that if the bend of the lead is calculated in accordance with the above-described algorithm, the lead bend is measured as being smaller than the actual lead bend, thereby giving rise to an erroneous determination in the determination of the non-defective or defective state. This is a problem in the conventional lead-bend measuring apparatus, to be solved by the invention.

SUMMARY OF THE INVENTION

It is, therefore, an object of the present invention to provide a lead-bend measuring apparatus capable of effecting accurate measurement by making improvements on the binarization processing of a plurality of divided lead portions.

To this end, in accordance with the present invention, there is provided a lead-bend measuring apparatus comprising:

an illuminating means for projecting light onto leads projecting from a package of an integrated circuit device;

an imaging means for imaging light reflected from and transmitted through the leads;

a cutout means for fetching an image of the imaged light and dividing the image into a plurality of sections;

a binarization processing means for processing gradations of the image with different binarization levels for each of the divided sections;

a profile counter means for preparing profiles of various portions of the leads corresponding to the respective sections from binarized data subjected to processing by the binarization processing means;

a calculating means for calculating a deviation of each of the prepared profiles from a reference profile and determining an amount of bend of each of the leads; and a means for determining a non-defective or defective state by making a comparison between the amount of bent calculated and allowable values.

BRIEF DESCRIPTION OF THE DRAWINGS

The above and other objects, features and advantages of the present invention will become more apparent from the following description of the invention when read in conjunction with the accompanying drawings, in which:

FIGS. 4A to 4F are diagrams for explaining the problem of the prior art lead-bend measuring apparatus, in which FIGS. 4A to 4D are graphs illustrating the distribution of illuminance at gradations, while FIGS. 4E to 4F are diagrams illustrating the positions of sections in the leads;

DESCRIPTION OF THE PREFERRED EMBODIMENTS

Now, preferred embodiments according to the invention are explained with reference to the accompanying drawings. It is to be noted that, throughout the following explanation, the same or similar numerals refer to the same or like elements in all the figures of the drawings.

Figure 1:
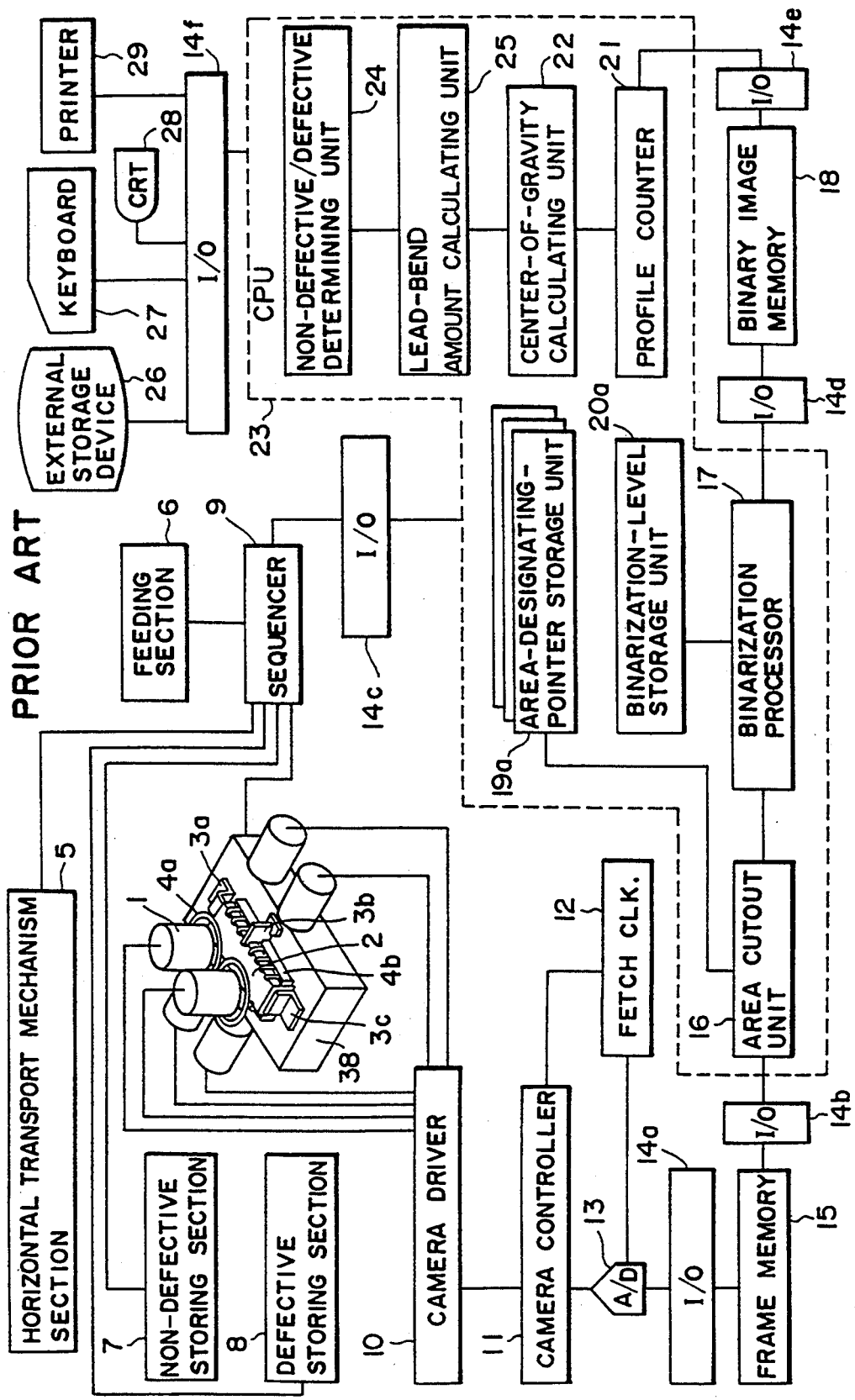
FIG. 1 is a block diagram of a prior art example of the lead-bend measuring apparatus.
Figure 2:
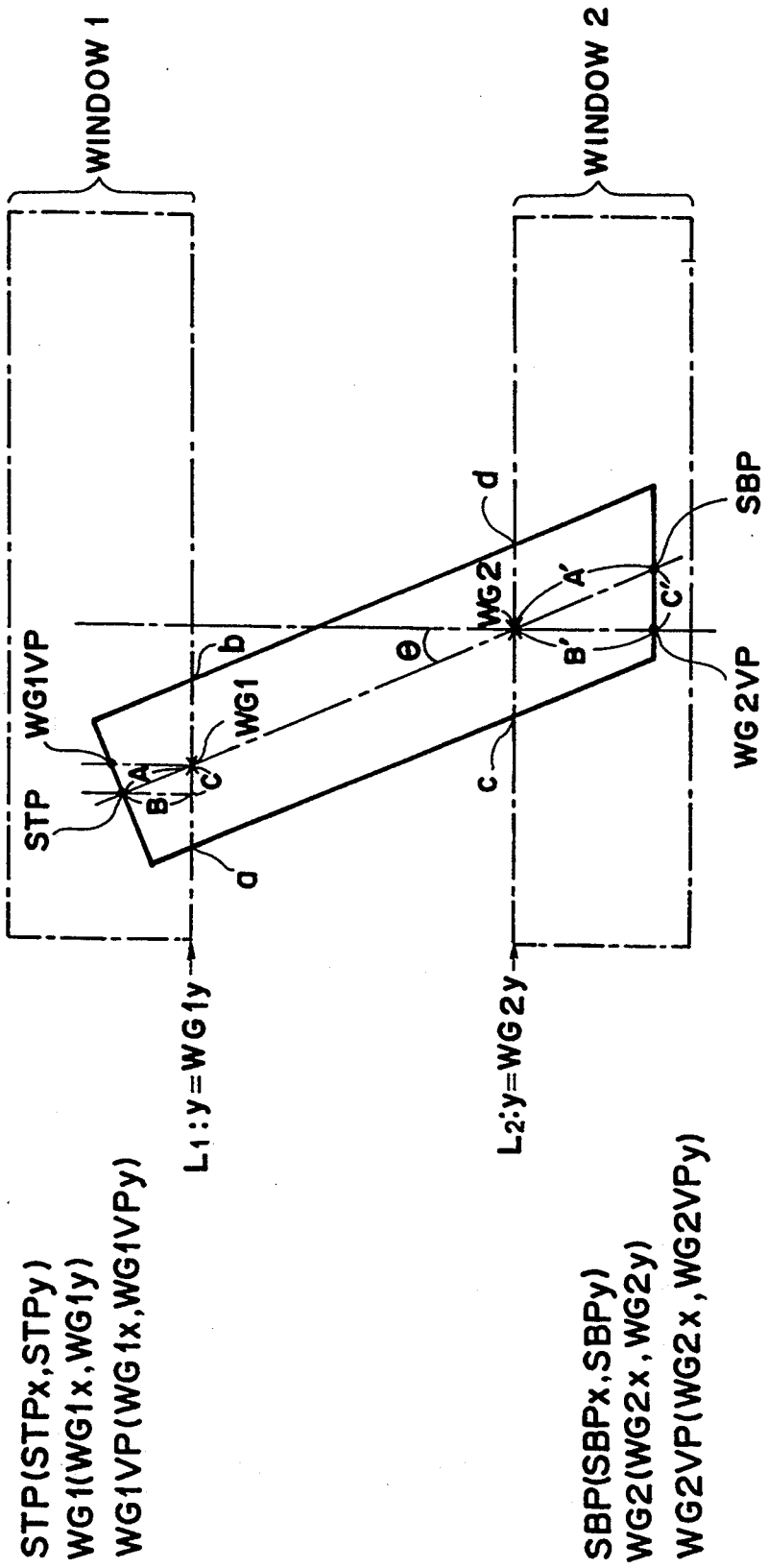
FIG. 2 As a diagram illustrating an algorithm for calculating an amount of bend in the lead-bend measuring apparatus shown in FIG. 1.
Figure 3C:
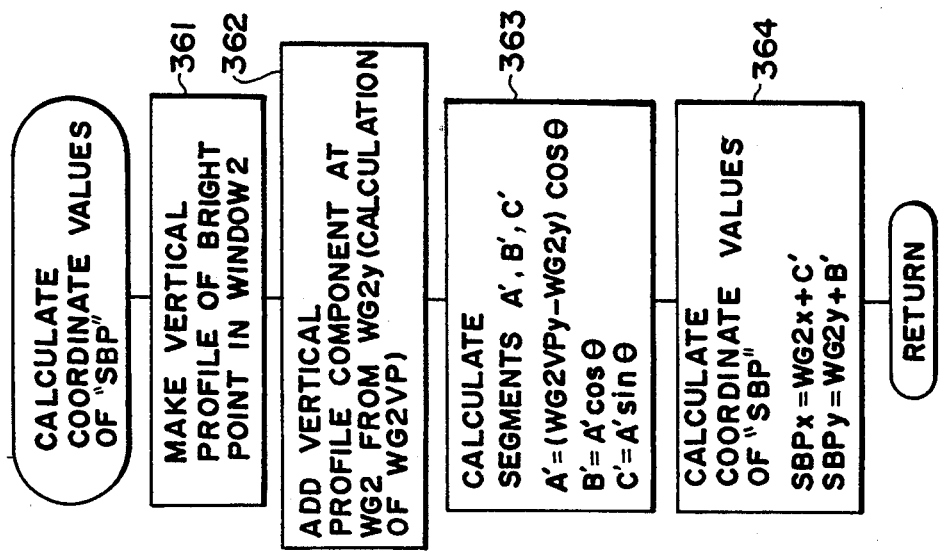
FIGS. 3A to 3C are flow-charts illustrating the algorithm.
Figure 3B:
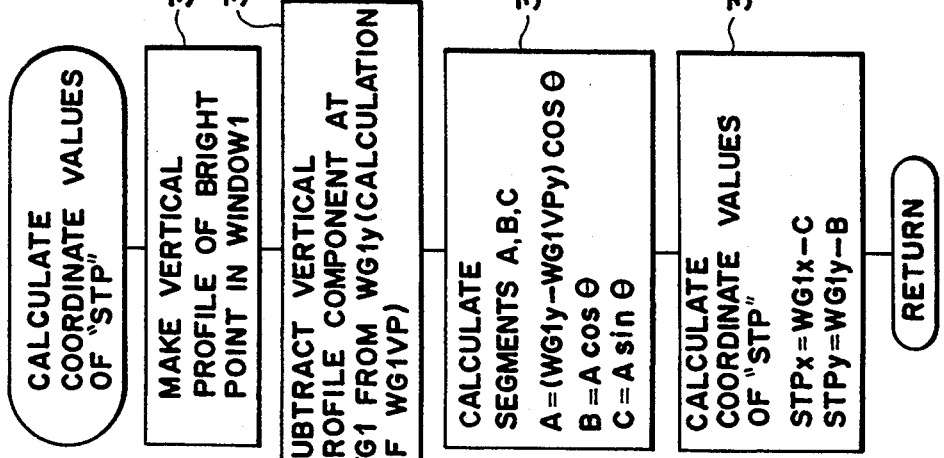
Figure 3A:
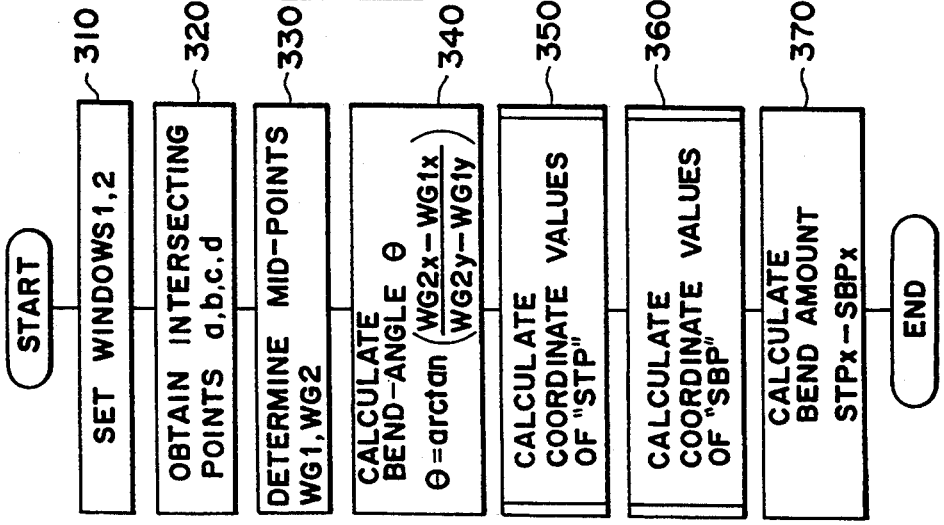
Figure 5:
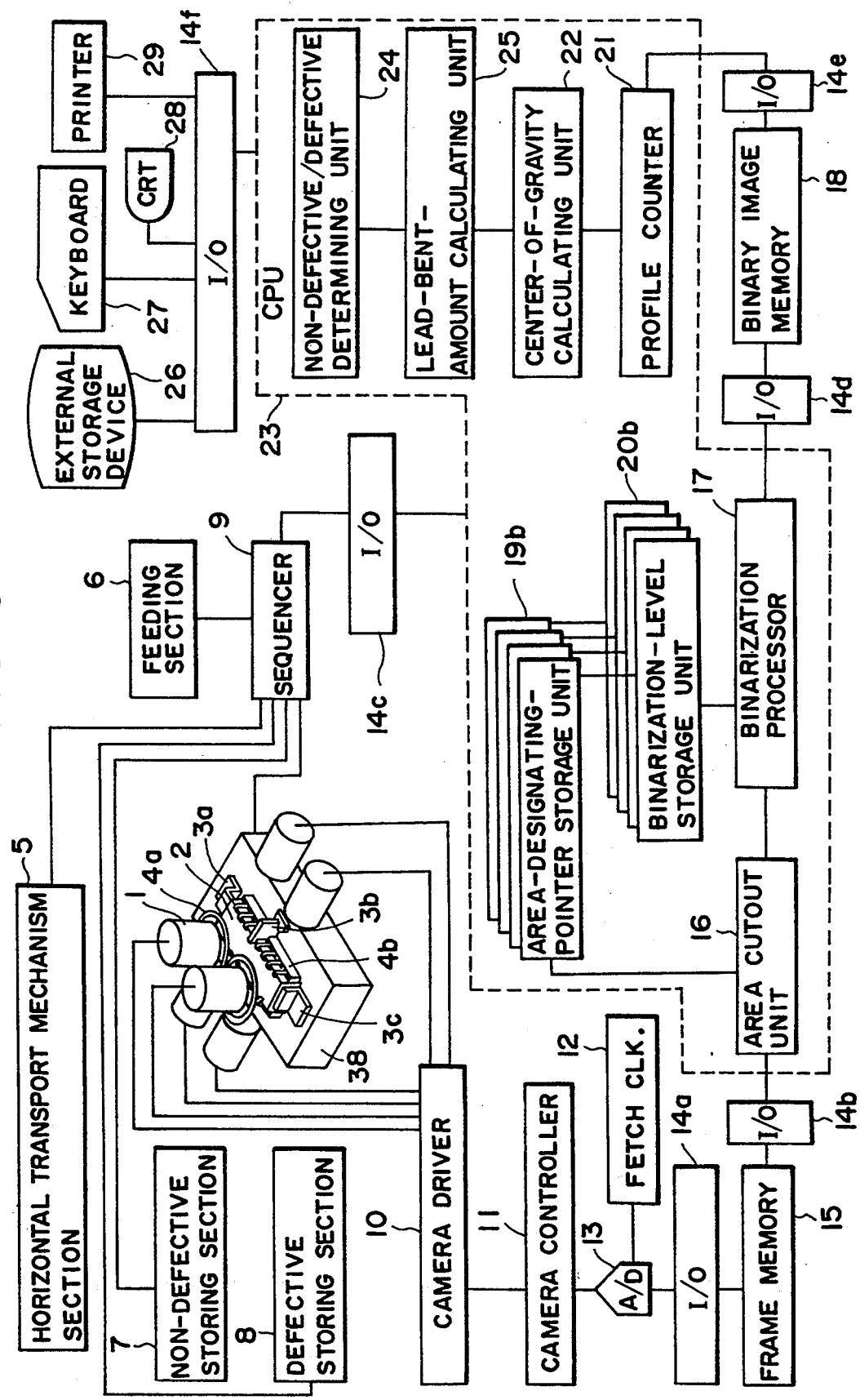
FIG. 5 is a block diagram of a lead-bend measuring apparatus in accordance with an embodiment of the present invention.
Figure 6A:
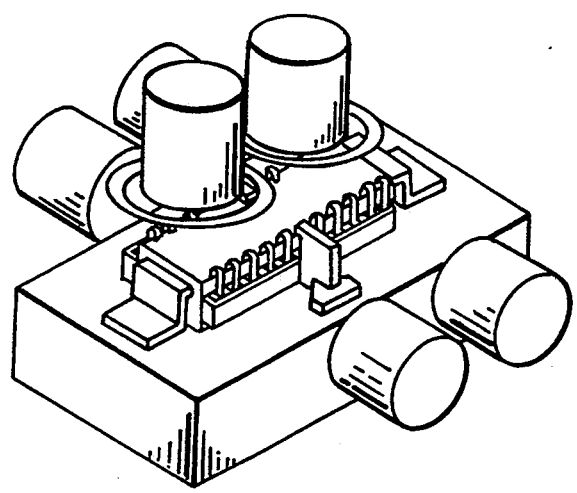
FIGS. 6A and 6B are enlarged perspective views of an inspection stage of the lead-bend measuring apparatus shown in FIG. 5.
Figure 6B:
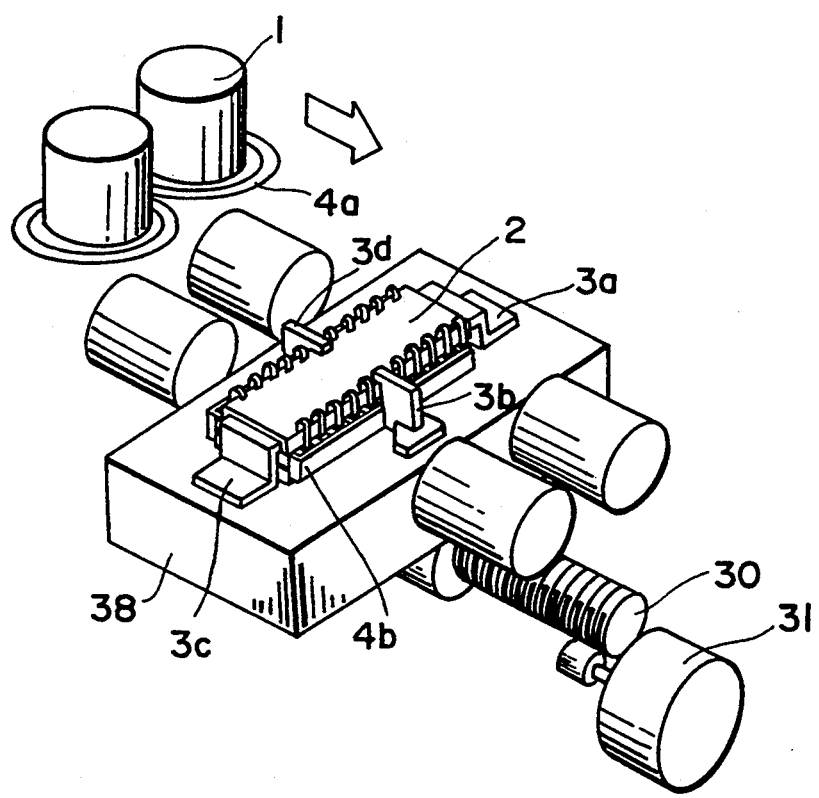
Figure 7:
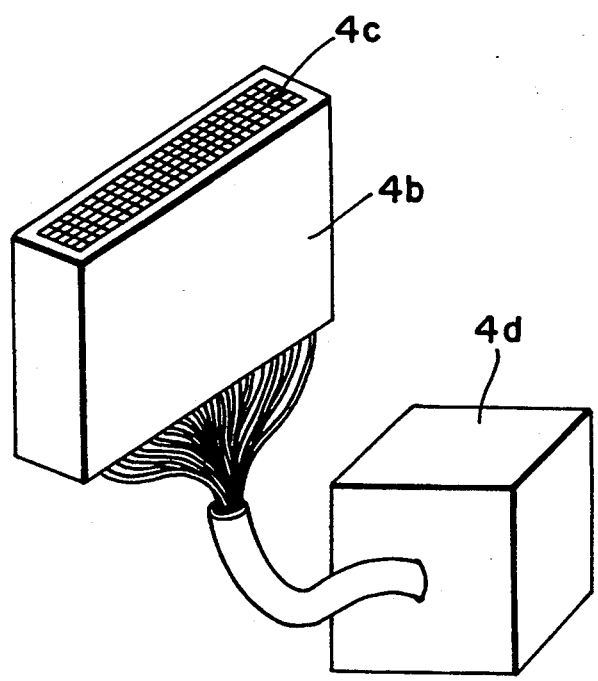
FIG. 7 is a perspective view of a lower illuminating means for illuminating lead portions in the lead-bend measuring apparatus shown in FIG. 5.

FIG. 5 is a block diagram of a lead-bend measuring apparatus in accordance with an embodiment of the present invention; FIGS. 6A and 6B are enlarged perspective views of an inspection stage of the lead-bend measuring apparatus shown in FIG. 5; and FIG. 7 is a perspective view of a lower illuminating means for illuminating lead portions in the lead-bend measuring apparatus shown in FIG. 5.

It should be noted that this lead-bend measuring apparatus is provided with binarization-level storage units 20b for storing the same number of binarization levels as the number of sections divided by an area cutout unit 16, as shown in FIG. 5. The lead-bend measuring apparatus of the present invention provided with the binarization-level storage units 20b is characterized in that clearer profiles of lead portions can be obtained as the binarization level selected for the dark and bright spots is changed in correspondence with the distribution of illuminance of light reflected from these sections.

A description will now be given of the operation of this lead-bend measuring apparatus. First, an IC 2 in FIG. 5 is gripped by a suction chuck of a horizontal transport mechanism section 5 which is controlled by a sequencer 9. The IC 2 is then moved horizontally and is transported from a feeding section 6 to an inspection stage 38. Then, as shown in FIG. 6, the IC 2 is placed on the inspection stage 38 with its rear surface facing upward, and is sucked with a vacuum so as to effect pre-alignment. The IC 2 is then fixed by means of a plurality of clamp claws 3a, 3b, 3c and 3d. The inspection stage 38 arranged in the state shown in FIG. 6B is fed by a ball screw 30, and the IC 2 is positioned below a pair of annular incandescent lamps 4a, as shown in FIG. 6A. Then, the distal ends of the leads of the IC 2 and flat apex portions at their tops are irradiated by the annular incandescent lamps 4a, while the proximal ends of the leads are irradiated by a pair of optical fiber arrays 4b each comprised of optical fibers 4c and connected to an incandescent lamp-house 4d, as shown in FIG. 7.

Subsequently, as shown in FIG. 5, a pair of camera heads 1, a camera driver 10, and a camera controller 11 image the reflected images obtained thereby, and a fetch clock 12 and an 8-bit A/D converter 13 write the images to a frame memory 15 via I/O ports 14a with 256 gradations. It should be noted that all of the distal ends, flat apex portions at the tops, and the proximal ends of the leads are imaged as reflected images. Then, the area cutout unit 16 extracts a plurality of sections designated by area-designating-pointer storage units 19b, and divides the multivalued image data in the frame memory 15 into a plurality of sections. A binarization processing unit 17 fetches respective binarization levels corresponding to the sections from the binarization-level storage units 20b and effects binarization processing of the respective sections. The image data subjected to binarization processing is written to a binary image memory 18 via I/O ports 14d. Subsequently, an amount of bend of each lead is determined by a profile counter 21, an area-center-of-gravity calculating unit 22, and a lead-bend-amount calculating unit 25 by using the same algorithm as the one described for the prior art. The amount of bend of each lead thus calculated is compared with allowable values by a non-defective/defective determining unit 24 so as to determine the non-defective or defective state of the IC 2.

Figure 8:
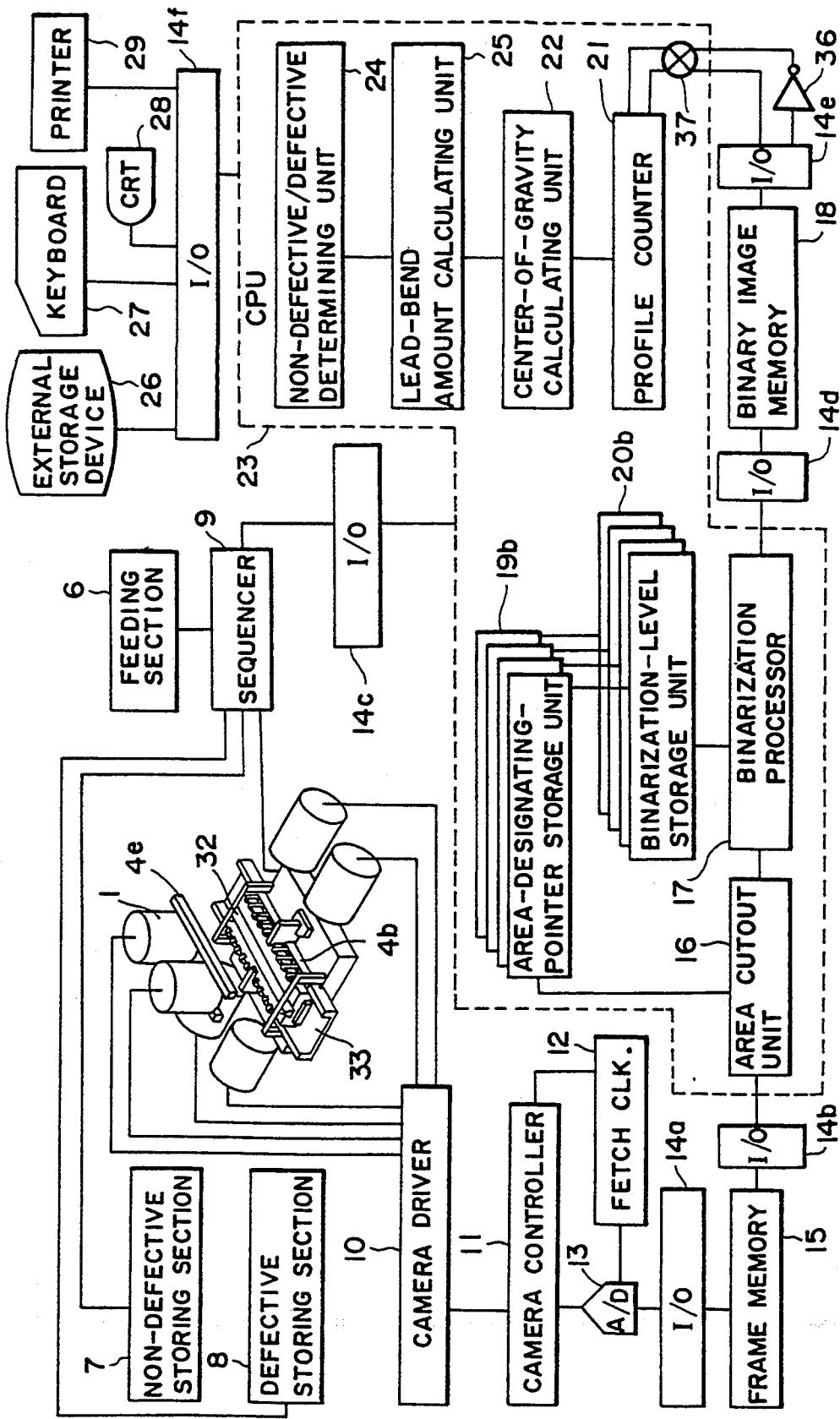
FIG. 8 is a block diagram of the lead-bend measuring apparatus in accordance with another embodiment of the present invention.
Figure 9:
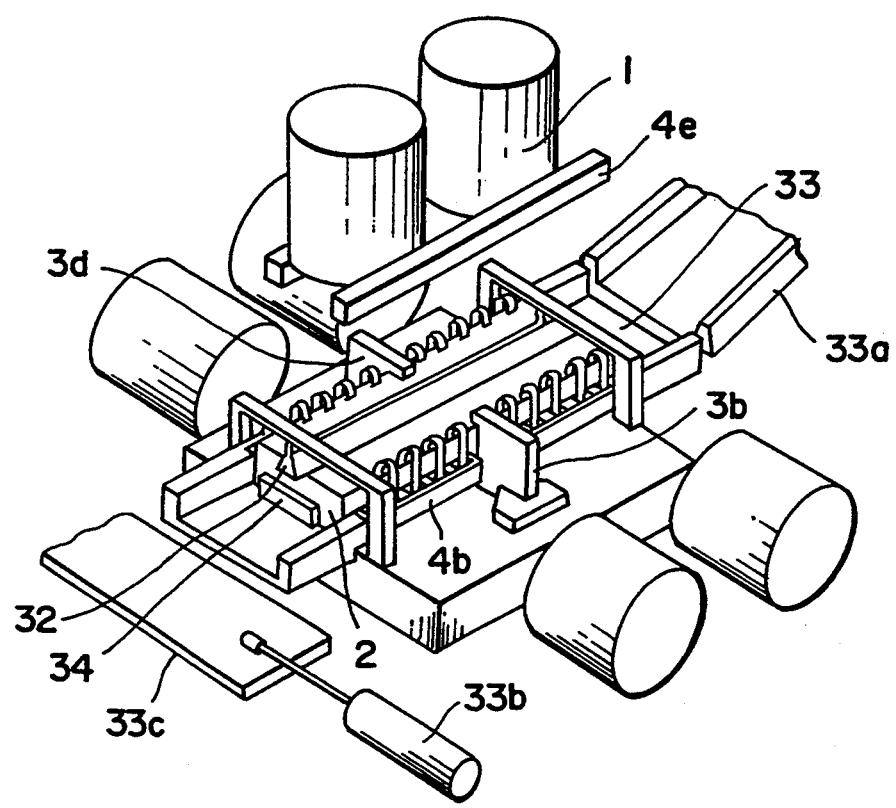
FIG. 9 is a perspective view of the inspection stage shown in FIG. 8 and an IC transport mechanism.

FIG. 8 is a block diagram of the lead-bend measuring apparatus in accordance with another embodiment of the present invention. FIG. 9 is a perspective view of the inspection stage shown in FIG. 8 and an IC transport mechanism. In this lead-bend measuring apparatus, a chute rail mechanism in which ICs are allowed to slide and drop by their own weight is adopted instead of the horizontal transport mechanism section which is used in the foregoing embodiment and in which each IC is gripped by a chuck and is moved. Namely, as shown in FIG. 9, this IC transport mechanism comprises a chute rail 33a having a groove along which the package of the IC slides from the feeding section 6 onto the inspection stage 38 (see FIG. 6B); a positioning rail 33 having a vertically movable positioning stopper 34 at one end side thereof, the positioning rail 33 being secured on the inspection stage; and a pusher 33b for allowing the IC 2 discharged onto a placing table 33c from the positioning rail 33 to be dropped into a non-defective storage section 7 or a defective storage section 8 after completion of the inspection.

As shown in FIG. 9, the illuminating means of this lead-bend measuring apparatus is arranged such that a pair of rod-like parallel light sources 4e are arranged above the IC 2 and in parallel with the direction in which the leads are arrayed, and a reflecting mirror 32 for reflecting the light from the rod-like parallel light sources 4e is disposed substantially in the center of the IC 2 so as to illuminate the apex portions of the leads projecting from both sides of the IC 2 with this reflected light. Accordingly, the apex portions of the leads are imaged as transmitted images, and the distal ends as reflected images. In addition, the proximal ends of the leads are illuminated by the optical fiber arrays 4b in the same way as in the foregoing embodiment, and are imaged as reflected images.

In the operation of this lead-bend measuring apparatus, the IC 2 is first fed from the feeding section 6 to the chute rail 33a, the IC 2 slides along the chute rail 33a and drops onto the positioning rail 33. As a result, a sensor (not shown) is operated, and the stopper 34 is raised to position the IC 2. The IC 2 is then fixed by means of the clamp claws 3b and 3d. Subsequently, the camera heads 1, the camera driver 10, and the camera controller 11 pick up images, and the fetch clock 12 and the 8-bit A/D converter 13 write the images to the frame memory 15 with 256 gradations via the I/O ports 14a. Then, the area cutout unit 16 cuts out the multivalued images into a plurality of sections designated by the area-designating-pointer storage units 19b. The binarization processing unit 17 then binarizes the cutout sections by using the binarization levels that are designated by the binarization-level storage units 20b on a one-to-one correspondence basis with respect to each section, and writes binarized image data to the binary image memory 18 through the I/O ports 14d. Here, which portions of the images stored in the frame memory 15 are to be cut out is automatically transferred from an external storage unit 26 to the area-designating-pointer storage units 19b and is stored therein at the start of the apparatus. In addition, an operator of the apparatus is capable of newly preparing or revising these area-designating-pointer storage units 19b freely by operating a keyboard 27.

Returning to the description of the operation, the profile counter 21, the area-center-of-gravity calculating unit 22, and the lead-bend-amount calculating unit 25 calculate the amounts of bend of all the leads of the IC 2 on the basis of the binarized images which have been read through I/O ports 14e in accordance with the lead-bend calculating algorithm. The non-defective/defective determining unit 24 determines the non-defective or defective state by making a comparison with allowable values. The IC 2 for which the determination has been completed is discharged onto the placing table 33c from the positioning rail 33, and is transported to the non-defective storage section 7 or the defective storage section 7 by the pusher 33b.

Since the apex portions of the leads are imaged as transmitted images, i.e., since images of the apex portions are stored in the binary image memory 18 as dark spots, the dark spots are converted to bright spots via an inverter 36 before they are fetched or loaded to the profile counter 21. The other portions of the leads, i.e., the distal and proximal ends of the leads, are recorded in the binary image memory 18 as reflected images, i.e., bright spots, so that the image data thereof are processed as they are by the profile counter 21. A software switch 37 of a CPU 23 manages both an input line with the inverter 36 and a line without the same, and performs switching in such a manner as to effect inverted inputting with respect to the processing of the apex portions of the leads and non-inverted inputting with respect to the distal and proximal ends of the leads.

In this embodiment, since images of the apex portions of the leads are fetched as transmitted images, the apex portions of the leads can be imaged more clearly as compared with the earlier explained embodiment in which images of the apex portions are fetched as reflected images. Hence, there is an advantage in that measurements can be effected with higher accuracy. In addition, there is an advantage in that the IC mechanism for transporting the ICs 2 is inexpensive. Furthermore, there is another advantage in that, since rod-like parallel light sources disposed in parallel with the direction in which the leads are arrayed are used as the illuminating means, the illuminance for the leads can be made more uniform.

As described above, in accordance with the present invention, there are provided the means for dividing the images of the leads into a plurality of sections and the means for setting binarization levels respectively corresponding to the divided sections and processing the sections with the corresponding binarization levels. Accordingly, there is an advantage in that even if the illuminance of the various portions of the leads is not uniform, it is possible to obtain clearer binarized images, thereby making it possible to effect measurements more accurately.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A lead-bend measuring apparatus comprising:
   illuminating means for projecting light onto leads projecting from a package of an integrated circuit device, said illuminating means including a reflecting mirror disposed substantially in a center of the integrated circuit device;
   imaging means for imaging light reflected from and transmitted through the leads;
   cutout means for fetching an image of the imaged light and dividing the image into a plurality of sections;
   binarization processing means for processing gradations of the image with different binarization levels for each of the divided sections, said binarization processing means including binarization level storing means for storing a same number of binarization levels as a number of the divided sections;
   profile counter means for preparing profiles of portions of the leads corresponding to the respective sections from binarized data subjected to processing by said binarization processing means;
   calculating means for calculating a deviation of each of the prepared profiles from a reference profile and determining an amount of bend of each of the leads; and
   means for determining a non-defective or defective state by making a comparison between the amount of bend calculated and allowable values.

2. A lead-bend measuring apparatus according to claim 1, wherein said illuminating means includes a pair of annular incandescent lamps for illuminating distal ends and apex portions of the leads and a pair of optical fiber arrays for illuminating proximal ends of the leads.

3. A lead-bend measuring apparatus according to claim 1, wherein said imaging means includes a pair of camera heads, a camera driver, and a camera controller for fetching the light reflected from and transmitted through the leads and for imaging distal ends, proximal ends, and apex portions of the leads.

4. A lead-bend measuring apparatus according to claim 1, wherein said cutout means includes an area cutout unit for cutting out the image into the plurality of sections and area-designating-pointer storage units for designating the sections to be cut out by said area cutout unit.

5. A lead-bend measuring apparatus according to claim 1, wherein said binarization processing means includes a binarization processing unit for fetching binarization levels corresponding to the divided sections and effecting binarization processing of the divided sections, wherein said binarization-level storing means comprises a plurality of binarization-level storage units for respectively storing the same number of binarization levels as the number of sections divided by said cutout means such that a number of binarization-level storage units corresponds to the number of sections divided by said cutout means.

6. A lead bend measuring apparatus according to claim 1, further comprising a transport mechanism for transporting the integrated circuit device to a non-defective storing section or a defective storing section after a non-defective or defective state of the integrated circuit device is determined.

7. A lead-bend measuring apparatus according to claim 6, wherein said transport mechanism comprises a horizontal transport mechanism in which the integrated circuit device is gripped by a chuck and is moved thereby.

8. A lead-bend measuring apparatus according to claim 6, wherein said transport mechanism includes a chute rail having a groove along which the package of the integrated circuit device slides from a feeding section onto an inspection stage, a positioning rail having a vertically movable positioning stop end side thereof, and a pusher for allowing the integrated circuit device discharged onto a placing table from the positioning rail, to be dropped into the non-defective storing section for storing non-defective integrated circuit devices or the defective storing section for storing defective integrated circuit devices after completion of a measurement.

9. A lead-bend measuring apparatus according to claim 1, wherein said cutout means includes an area cutout unit for cutting out the image into the plurality of sections.

10. A lead-bend measuring apparatus according to claim 9, wherein said cutout means further includes area-designating-pointer storage units for designating the sections to be cut out by said area cutout unit.

11. A lead-bend measuring apparatus according to claim 10, wherein said binarization processing means includes a binarization processing unit for fetching binarization levels corresponding to the cutout sections and effecting binarization processing of the cutout sections.

12. A lead-bend measuring apparatus according to claim 11, wherein said binarization processor changes binarization levels for selected portions of said leads in correspondence with a distribution of illuminance of light reflected from said selected portions.

13. A lead-bend measuring apparatus comprising:
illuminating means for projecting light onto leads projecting from a package of an integrated circuit device, said illuminating means including a pair of rod-like parallel light sources arranged in parallel with a direction in which the leads are arrayed, and a reflecting mirror disposed substantially in a center of the integrated circuit device for reflecting the light from the rod-like parallel light sources so as to illuminate apex portions of the leads projecting from sides of the integrated circuit device;
imaging means for imaging light reflected from and transmitted through the leads;
cutout means for fetching an image of the imaged light and dividing the image into a plurality of sections;
binarization processing means for processing gradations of the image with different binarization levels for each of the divided sections, said binarization processing means including binarization-level storing means for storing a same number of binarization levels as a number of the divided sections;
profile counter means for preparing profiles of portions of the leads corresponding to the respective sections from binarized data subjected to processing by said binarization processing means;
calculating means for calculating a deviation of each of the prepared profiles from a reference profile and determining an amount of bend of each of the leads; and
means for determining a non-defective or defective state by making a comparison between the amount of bend calculated and allowable values.

14. A lead-bend measuring apparatus, comprising:
illuminating means for projecting light onto leads projecting from a package of an integrated circuit device, said illuminating means including a reflecting mirror disposed substantially in a center of the integrated circuit device;
imaging means for imaging light reflected from and transmitted through the leads;
cutout means for fetching an image of the imaged light and selectively dividing the image into a plurality of sections;
means for processing gradations of the image with binarization levels selectively set for each of the divided sections according to the gradations, said processing means including binarization level storing means for storing a same number of binarization levels as a number of the divided sections;
bend-amount determining means for determining an amount of bend of said leads based on an output of said processing means;
means for storing predetermined values representing an allowable amount of bend of said leads; and
means for determining a non-defective or defective state based on a comparison between the amount of bend determined by said bend-amount determining means calculated and allowable values.

15. A lead-bend measuring apparatus according to claim 14, wherein said illuminating means includes a plurality of lamps for illuminating distal ends and apex portions of the leads and a pair of optical fiber arrays for illuminating proximal ends of the leads.

16. A lead-bend measuring apparatus according to claim 14, wherein said imaging means includes a pair of camera heads, a camera driver, and a camera controller for fetching the light reflected from and transmitted through the leads and for imaging distal ends, proximal ends, and apex portions of the leads.

17. A lead-bend measuring apparatus according to claim 14, wherein said cutout means includes an area cutout unit for cutting out the image into the plurality of sections and area-designating-pointer storage units for designating the sections to be cut out by said area cutout unit.

18. A lead-bend measuring apparatus according to claim 17, wherein said processing means includes a binarization processing unit for fetching binarization levels corresponding to the divided sections and effecting binarization processing of the cutout sections, wherein said binarization level storing means comprises a plurality of binarization-level storage units for respectively storing the same number of binarization levels as the number of sections divided by said cutout means such that a number of binarization levels storage units corresponds to the number of sections divided by said cutout means.

19. A lead-bend measuring apparatus according to claim 14, wherein said processing means includes a binarization processing unit for fetching binarization levels corresponding to the divided sections and effecting binarization processing of the cutout sections, wherein said binarization level storing means comprises a plurality of binarization-level storage units for respectively storing the same number of binarization levels as the number of sections divided by said cutout means such that a number of binarization levels storage units corresponds to the number of sections divided by said cutout means.

20. A lead-bend measuring apparatus comprising:
illuminating means for projecting light onto leads projecting from a package of an integrated circuit device, said illuminating means including a pair of light sources arranged in parallel with a direction in which the leads are arrayed, and a reflecting mirror disposed substantially in a center of the integrated circuit device for reflecting the light from the light sources so as to illuminate apex portions of the leads projecting from sides of the integrated circuit device;

imaging means for imagine light reflected from and transmitted through the leads;

cutout means for fetching an image of the imaged light and selectively dividing the image into a plurality of sections;

means for processing gradations of the image with binarization levels selectively set for each of the divided sections according to the gradations, said processing means including binarization level storing means for storing a same number of binarization levels as a number of the divided sections;

bend-amount determining means for determining an amount of bend of said leads based on an output of said processing means;

means for storing predetermined values representing an allowable amount of bend of said leads; and means for determining a non-defective or defective state based on a comparison between the amount of bend determined by said bend-amount determining means calculated and allowable values.

* * * * *